United States Patent [19]
Bell et al.

[11] Patent Number: 4,677,113
[45] Date of Patent: Jun. 30, 1987

[54] DI-T-BUTYLPHENOLS SUBSTITUTED BY A THENOYL GROUP

[75] Inventors: Randy L. Bell, North St. Paul; George G. I. Moore, Woodbury, both of Minn.

[73] Assignee: Riker Laboratories, Inc., St. Paul, Minn.

[21] Appl. No.: 854,846

[22] Filed: Apr. 22, 1986

[51] Int. Cl.$^4$ ................... A61K 31/38; C07D 333/38
[52] U.S. Cl. ..................... 514/448; 549/61; 549/70; 549/71; 549/72
[58] Field of Search ............ 549/71, 72, 70, 61; 514/448

[56] References Cited

U.S. PATENT DOCUMENTS

| 4,131,682 | 12/1978 | Evans et al. | 549/70 |
| 4,172,082 | 10/1979 | Moore | 549/72 |
| 4,179,515 | 12/1979 | Mieville | 514/448 |
| 4,198,519 | 4/1980 | Goudie | 549/70 |

FOREIGN PATENT DOCUMENTS 0070685  4/1984  Japan ................. 549/70

Primary Examiner—Alan Siegel
Attorney, Agent, or Firm—Donald M. Sell; James A. Smith; Robert W. Sprague

[57] ABSTRACT

Novel compounds which are 2,6-di-t-butylphenols substituted on the 4 position by a thenoyl group, which thenoyl group is substituted by an acid group are useful as inhibitors of leukotriene synthesis and as antiallergic agents.

9 Claims, No Drawings

DI-T-BUTYLPHENOLS SUBSTITUTED BY A THENOYL GROUP

TECHNICAL FIELD

This invention relates to compounds which are inhibitors of leukotriene synthesis. This invention further relates to pharmacological methods of using such compounds, pharmaceutical compositions containing such compounds and synthetic intermediates for preparing such compounds.

BACKGROUND OF THE INVENTION

The leukotrienes are a novel group of biologically active mediators derived from arachidonic acid through the action of lipoxygenase enzyme systems. The leukotrienes are potent smooth muscle contracting agents, particularly on respiratory smooth muscle but also on other tissues. In addition, they promote mucous production, modulate vascular permeability changes and are potent inflammatory mediators in human skin. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The most important compound in the second group of leukotrienes, namely dihydroxy fatty acids, is Leukotriene $B_4$. This compound is a potent chemotactic agent for neutrophils and eosinophils, and, in addition, may modulate a number of other functions of these cells. It also affects other cell types such as lymphocytes and, for example, may modulate the action of suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a lipoxygenase enzyme. See, for example, D. M. Bailey et al., Ann. Rpts. Med. Chem. 17 203 (1982).

RESPIRATORY CONDITIONS

Asthma The leukotrienes are potent spasmogens of human trachea, bronchus and lung parenchymal strips, and, when administered to normal volunteers as aerosols, are 3,800 times more potent than histamine in inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs. Lipoxygenase products are also thought to be regulators of mast cell degranulation, and recent studies with human lung mast cells have suggested that lipoxygenase inhibitors, but not corticosteroids, may suppress antigen-induced mast cell degranulation. In vitro studies have shown that antigen challenge of human lung results in the release of leukotrienes, and in addition, purified human mast cells can produce substantial amounts of leukotrienes. There is, therefore, good evidence that the leukotrienes are important mediators of human asthma. Lipoxygenase inhibitors would, therefore, be a new class of drugs for the treatment of asthma. See for example, B. Samuelsson, Science 220 568-575 (1983).

SKIN DISEASES

Psoriasis Psoriasis is a human skin disease which affects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in pronounced neutrophil accumulations. There are gross abnormalities in arachidonic acid metabolism in human psoriatic skin. In particular, highly elevated levels of free arachidonic acid can be measured, as well as large amounts of lipoxygenase products. Leukotriene $B_4$ has been detected in psoriatic lesions, but not in uninvolved skin, in biologically significant amounts.

ALLERGIC CONDITIONS

Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes. Leukotrienes can also mediate other diseases. These include atopic dermatitis, gouty arthritis, gall bladder spasms and ulceritive colitis. In addition, they may have a role in cardiovascular disease because Leukotrienes $C_4$ and $D_4$ act as coronary and cerebral arterial vasoconstrictors and these compounds may also have negative inotropic effects on the myocardium. In addition, the leukotrienes are important mediators of inflammatory disease through their ability to modulate leukocyte and lymphocyte function.

Many substituted di-t-butylphenols are known. Generally, these compounds may be useful as antioxidants. Some of these compounds are also known to be active antiinflammatory agents.

Compounds wherein 2,6-di-t-butylphenol is substituted in the 4-position by an unsubstituted thenoyl group or certain simply substituted thenoyl groups are known. For example, see U.S. Pat. No. 4,172,082 and references cited therein.

No compounds are known wherein a 2,6di-t-butylphenol is substituted in the 4-position by a thenoyl group wherein such thenoyl group is substituted by a carboxyl group.

SUMMARY OF THE INVENTION

The present invention relates to novel antiallergic compounds of Formula I:

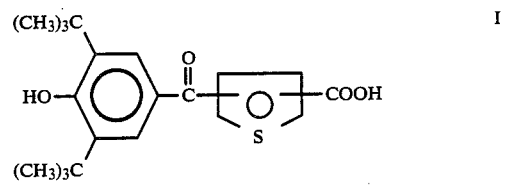

and carboxylate derivatives thereof selected from lower alkyl esters, (lower)alkylamino(lower)alkyl esters, pharmaceutically acceptable (lower)alkylamino(lower)alkyl ester acid-addition salts and pharmaceutically acceptable carboxylate salts. These compounds are useful as inhibitors of mamalian leukotriene biosynthesis, and, as such, are useful therapeutic agents for treating allergic conditions, particularly asthma. This invention also relates to pharmacological methods for using compounds of Formula I and pharmaceutical compositions containing such compounds.

The present invention also relates to novel compounds of Formula II:

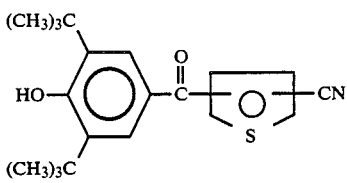

These compounds are useful synthetic intermediates for preparing compounds of Formula I.

DETAILED DESCRIPTION OF THE INVENTION

By "lower" as used in connection with "alkyl", it is meant that such groups contain one to about four carbon atoms. Most preferred alkyl groups contain one to two carbon atoms.

Presently preferred are compounds of Formula I wherein the linking carbonyl is bonded to the 2-position of the thiophene ring, and the carboxyl group is on the 5-position of the thiophene ring.

Compounds of Formula I of the invention may be prepared according to Scheme A below:

Scheme A

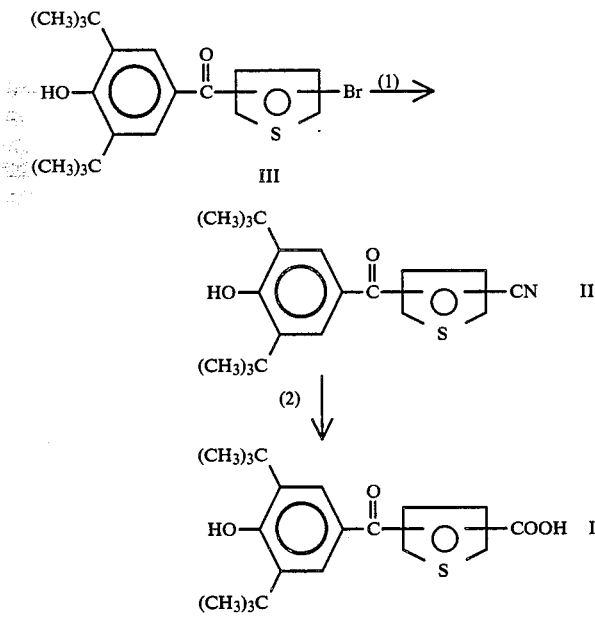

Step (1) of Scheme A involves the reaction of the intermediate of Formula III with a metal cyanide salt, preferably cuprous cyanide, in a solvent such as pyridine, N-methylpyrrolidone or quinoline to provide a novel intermediate of Formula II.

In Step (2) of Scheme A, the intermediate of Formula II is hydrolyzed to convert the cyano group to carboxyl and to thereby provide a compound of Formula I. This hydrolysis reaction can be carried out using acid or base. Hydrolysis using an excess of a moderately concentrated inorganic base such as sodium hydroxide is preferred. The mixture is diluted with a solvent which is suitable to effect dissolution of the intermediate of Formula II such as a lower alcohol. The mixture is then heated at its reflux temperature until the intermediate of Formula II has been reacted. The products of Formula I are readily isolated by conventional methods.

The starting compounds of Formula III wherein the linking carbonyl group is bonded to the 2-position of the thiophene ring may be prepared via a standard Friedel-Crafts reaction of the known compound 3,5-di-t-butyl-4-hydroxybenzoyl chloride with known 2- or 3-bromothiophene. The reaction is conducted in the presence of a strong Lewis acid such as aluminum chloride or titanium tetrachloride as a catalyst.

The starting compounds of Formula III wherein the linking carbonyl group is bonded to the 3-position of the thiophene ring may be prepared via the standard Friedel-Crafts reaction of known 2,6-di-t-butylphenol with a bromothiophene-3-carbonyl chloride. A weaker catalyst such as titanium tetrachloride will be preferred if the reaction rate is too rapid with aluminum chloride. The bromothiophenecarbonyl chlorides are known or may be prepared by conventional methods from the corresponding bromothiophenecarboxylic acids. This method can also be used to prepare compounds of Formula III wherein the linking carbonyl is bonded to the 2-position of the thiophene ring.

Compounds of Formula III may also be prepared by direct bromination of the known compounds 2,6-di-t-butyl-4-(2'- or 3'-thenoyl)phenol.

In an alternative process to that illustrated in Scheme A, compounds of Formula I may also be prepared by the lithiation of known 2,6-di-t-butyl-4-(2' or 3'-thenoyl)phenol, followed by treatment with carbon dioxide and quenching with acid.

It is well known to the art that pharmaceutically acceptable salts such as alkali metal, alkaline earth, aluminum and other metal and amine salts of pharmaceutically active acids are the equivalents of the acids in the terms of activity, and in some cases, may even offer advantages in absorption, formulation and the like. Pharmaceutically-acceptable carboxylate salts of the free acid compounds of the invention are prepared by reaction of the acid with a base and subsequent evaporation to dryness, preferably under mild conditions. The base may be organic, for example, sodium methoxide or an amine, or inorganic, for example, sodium hydroxide. Alternatively, the cation of a carboxylate salt, for example, sodium, may be displaced by a second cation such as calcium or magnesium when the salt of the second cation is more insoluble in a selected solvent.

Other useful derivatives of the compounds of Formula I include the alkyl esters, alkylaminoalkyl esters and salts. In the ester derivatives, the hydrogen portion of the carboxylic acid group is replaced with an alkyl or substituted alkyl.

Ester derivatives may be obtained by alkylation of an alkali metal salt of the compound in N,N-dimethylformamide with an alkyl iodide or dialkylaminoalkyl chloride.

The antiallergic biological activity of the compounds of Formula I generally may be demonstrated via a variety of assays including in vitro assays for measuring inhibition of lipoxygenase activity and leukotriene synthesis, and in vivo assays for inhibiting bronchoconstriction. The compound 5-(3′,5′-di-t-butyl-4′-hydroxybenzoyl)thiophene-2-carboxylic acid has been tested as described below and has been found to exhibit antiallergic activity.

More specifically, a suitable assay for demonstrating inhibition of lipoxygenase activity by the Compounds of Formula I utilizes lipoxygenase isolated from mammalian lung tissue, e.g., the lung tissue of guinea pigs is used. An example of such an assay is that described by Ben Aziz, et al., Anal. Biochem. 34, 88 (1970), incorporated herein by reference. The inhibition of lipoxygenase activity is measured by a rapid and sensitive spectrophotometric technique.

The activity of the compounds of Formula I may also be demonstrated in a more specific test for leukotriene inhibition. This test utilizes the cell free leukotriene biosynthesis system of M. Steinhoff et al. Biochim. Acta. 68, 28 (1980), incorporated herein by reference, which consists of homogenized rat basophil leukemia cells. Leukotriene synthesis is initiated by the addition of arachidonate. Solutions are centrifuged and supernatants assayed using a radioimmunoassay developed as described by Aeringhaus et al. FEBS Letter 146, 111-114. Drugs are dissolved in ethanol or dimethyl sulfoxide and then preincubated for five minutes. Phenidone is used as a positive control. The compound 5-(3′,5′-di-t-butyl-4′-hydroxybenzoyl)thiophene-2-carboxylic acid of the invention exhibits an $IC_{50}$ at a concentration of 15 micromolar.

The compounds of Formula I are relatively inactive as inhibitors of cyclooxygenase. This is important in order to obtain in vivo antiallergic activity. A convenient in vitro method for measuring cyclooxygenase activity is an assay wherein the amount of thromboxane $B_2$ production is measured in a whole human blood clotting assay. The thromoboxane $B_2$ production is measured by a radioimmunoassay as described by Patrono, et al., Thromb. Res. 17, 317 (1980), incorporated herein by reference.

The in vivo test used to demonstrate antiallergic activity of the compounds of Formula I may be any of those known to those skilled in the art. Preferably, bronchoconstriction in sensitized guinea pigs is measured upon antigen challenge. This test is described in broad terms by Piechuta, et al., Immunology, 38, 385 (1979) and more specifically by Hammerbeck and Swingle, Int. Archs. Allergy Appl. Immun. 74, 84-90 (1984), both references being incorporated herein by reference. It was used in a modified form as follows: Male Hartley guinea pigs (250-600 g) which were pretreated with an antihistamine, e.g., chlorpheniramine and then dosed intraperitoneally with a compound of the invention at a level of about 1 to 40 mg/kg 15 minutes prior to challenge or orally at the same dose 30 minutes prior to challenge were aerosol challenged with either water or ovalbumim at a concentration of 10 mg per ml. The animals were placed under an inverted dessicator jar ($18 \times 14$ cm) with a constant flow of air coming into the chamber from a compressed-air source to prevent hypoxia. Air flow leaving the chamber and fluctuations due to respiration were monitored through a separate outlet with a Fleisch No. 0000 pneumotachograph (available from Beckman Instruments, Inc., Schiller Park, Ill.) coupled to a Beckman Type R dynograph (available from Beckman Instruments, Inc.). Aerosolization through a third outlet was made via a No. 4 DeVilbiss nebulizer (available from the DeVilbiss Company, Somerset, PA) for 90 seconds at 150 mm Hg. The characteristic respiratory patterns observed were summations of two air exchange processes occurring simultaneously in the chamber. One exchange process was due to inspiration and expiration of air into and out of the animal, while the other exchange process was due to the air flow into and out of the chamber due to respiratory movements. The tracing obtained was the mechanical representation of the summation of those flows. Superimposed on the tracings was a characteristic spiking ('notching'), which appears to be an exaggerated expiratory movement, the frequency of which correlates with the severity of the bronchoconstrictive reaction. The frequency of notching for 15-minute periods beginning 4 minutes after the beginning of the aerosol challenge was used for comparing various treatments. Effects are considered significant if the t value achieved $p<0.05$. The compound 5-(3′,5′-di-t-butyl-4′-hydroxybenzoyl)-thiophene-2-carboxylic acid exhibits as $ED_{40}$ of less than 10 mg/kg when administered intraperitoneally, and an $ED_{40}$ of less than 25 mg/kg when administered orally.

The pharmaceutical compositions of the present invention will contain sufficient compound of Formula I in a dosage form suitable for inhibiting the mammalian biosynthesis of leukotrienes, or for the treatment desired. The effective concentration of the Formula I compound in the composition will vary as required by the mode of administration, dosage form and pharmacological effect and level desired.

For treating pulmonary conditions such as asthma, the mode of administration may be oral, parenteral, by inhalation, by suppository and the like. Suitable oral dosage forms are tablets, elixirs, emulsions, solutions, capsules, including delayed or sustained release dosage forms. Dosage forms for administration by inhalation include aerosols and sprays and may be administered in metered doses.

For treating allergies or allergic reactions, the compound of Formula I may be administered by any conventional mode, e.g., orally, parenterally, topically, subcutaneously, by inhalation and the like. The oral and parenteral dosage forms are as described for pulmonary treatment. The topical application dosage forms include ointments, sprays, controlled release patches, powders, solutions and the like.

For treating inflammation, the mode of administration may be oral, parenteral, by suppository and the like. The various dosage forms are as described above.

For treating skin diseases such as psoriasis, atopic dermatitis and the like, oral, topical or parenteral administration is useful. For topical application to the diseased area, salves, patches, controlled release patches, emulsions, etc. are convenient dosage forms.

For treating cardiovascular conditions, any suitable mode of administration such as oral or intraperitoneal may be used.

In addition to the common dosage forms listed above, the compounds of Formula I may also be administered various utilities and indications or for inhibiting leukotriene synthesis by controlled release means and/or delivery devices.

In preparing suitable dosage forms, conventional compounding procedures and ingredients, e.g., diluents, carriers, etc. may be used. Examples of suitable solid carriers are lactose, terra alba, sucrose, talc, gelatin, agar, pectin, acacia, magnesium stearate, stearic acid, and the like. Examples of suitable liquid carriers are syrup, peanut oil, olive oil, water and the like. Similarly, the carrier or diluent can include any time delay material well known to the art, such as glyceryl monostearate or glyceryl distearate, these being useful alone or, for example, in combination with wax.

The following examples are provided to illustrate the invention, but are not intended to limit the invention.

EXAMPLE 1

Synthesis of 5-(3,5-di-t-butyl-4-hydroxybenzoyl)-thiophene-2-carboxylic Acid.

Part A

Portions of 13.5 g of aluminum chloride were slowly added to a stirred solution of 26.9 g (0.10 mole) of 3,5-di-t-butyl-4-hydroxybenzoyl chloride in 300 ml of carbon disulfide. The mixture was warmed slightly, then 17.0 g (0.104 mole) of 2-bromothiophene was added dropwise. The reaction mixture was allowed to stir at room temperature for 48 hours, then poured into 10% hydrochloric acid. The resulting crude solid was collected and rinsed with petroleum ether and then treated with decolorizing charcoal and recrystallized from hexane to give 15.6 g of pale yellow 4-(5'-bromo-2'-thenoyl)-2,6-di-t-butylphenol, m.p. 126°–127.5° C.

Analysis: Calculated for $C_{19}H_{23}BrO_2S$: %C, 57.7; %H, 5.9. Found: %C, 57.6; %H, 5.9.

Part B

Under a nitrogen atmosphere, 271 g (0.686 mole) of 4-(5'-bromo-2'-thenoyl)-2,6-di-t-butylphenol was dissolved in 2 liters of pyridine, then 64.5 g (0.72 mole) of cuprous cyanide was added and the resulting mixture was heated at reflux for 30 hours. The pyridine was removed under vacuum and the residue shaken with 2 liters of 10% hydrochloric acid and 1 liter of methylene chloride. The resulting mixture was filtered to remove the inorganic salts, and the layers were separated. The organic layer was washed with 10% hydrochloric acid and water, then evaporated to give a crude solid which nuclear magnetic resonance spectral analysis showed to be a 1:1 mixture of the starting bromo compound and the cyano product. This material was dissolved in 3 liters of pyridine, then refluxed with 70 g of cuprous cyanide for 72 hours. The reaction was worked up as above to give a crude solid which was treated with decolorizing charcoal and recrystallized from 2.5 liters of ethanol to give a pale beige solid. 10 g of this material was dissolved in 450 ml of hot ethanol. The hot ethanol solution was filtered, then allowed to cool to give 2.2 g of pale yellow needles of 4-(5'-cyano-2'thenoyl)-2,6-di-t-butylphenol, m.p. 145.5°–147.5° C.

Analysis: Calculated for $C_{20}H_{23}NO_2S$: %C, 70.3; %H, 6.8; %N, 4.1. Found: %C, 70.7; %H, 6.9; %N, 4.0.

Part C

A mixture of 2 g of 4-(5'-cyano-2'-thenoyl)-2,6-di-t-butylphenol, ethanol and excess aqueous sodium hydroxide was heated at reflux for 1 hour. The reaction mixture was allowed to cool and then was acidified with 10% hydrochloric acid and extracted with methylene chloride. The extract was dried, then evaporated. The residue was triturated with hexane to give a crude yellow solid. The crude material was stirred with dilute sodium hydroxide, then filtered. The filtrate was acidified to give 1.9 g of a yellow solid. This material was dissolved in chloroform and then put on a column of silica gel. The column was eluted first with benzene and then with acetone. The acetone was evaporated to give an oil which was partitioned between hexane and dilute sodium hydroxide. The aqueous layer was acidified and chilled to give 1 g of a beige solid. This material was recrystallized from ethanol to give 0.8 g of off-white 5-(3',5'-di-t-butyl-4'-hydroxybenzoyl)thiophene-2-carboxylic acid, m.p. 228°–229.5° C.

Analysis: Calculated for $C_{20}H_{24}O_4S$: %C, 66.6; %H, 6.7. Found: %C, 66.9; %H, 6.9.

EXAMPLE 2

Synthesis of 2-(3',5'-di-t-butyl-4'-hydroxybenzoyl)thiophene-3-carboxylic acid.

Part A

Under a nitrogen atmosphere, 13.5 g (0.101 mole) of aluminum chloride was added in portions to a stirred solution of 26.8 g (0.10 mole) of 3,5-di-t-butyl-4-hydroxybenzoyl chloride in 250 ml of carbon disulfide. The reaction was stirred for 15 minutes and then a solution of 16.35 g (0.10 mole) of 3-bromothiophene in carbon disulfide was added dropwise over a period of about 20 minutes. The reaction was stirred for 8 hours, then poured into 10% hydrochloric acid. The resulting yellow oil was triturated with hexane containing a small amount of carbon tetrachloride, then chilled at −20° C. overnight to give an orange solid. This material was recrystallized four times from hexane with treatment with decolorizing charcoal to give 6.4 g of yellow 4-(3'-bromo-2'-thenoyl)-2,6-di-t-butylphenol, m.p. 116°–118° C., the structural assignment being confirmed by nuclear magnetic resonance analysis.

Analysis: Calculated for $C_{19}H_{23}BrO_2S$: %C, 58.2; %H, 5.8. Found: %C, 58.2; %H, 6.1.

Part B

Using the method of Part B in Example 1, the 4-(3'-bromo-2'-thenoyl)-2,6-di-t-butylphenol prepared in Part A above could be reacted with cuprous cyanide to give 4-(3'-cyano-2'-thenoyl)-2,6-di-t-butylphenol.

Part C

Using the general method of Part C in Example 1, 4-(3'-cyano-2'-thenoyl)-2,6-di-t-butylphenol prepared in Part B above could be hydrolyzed to give 2-(3,5-di-t-butyl-4-hydroxybenzoyl)thiophene-3-carboxylic acid.

EXAMPLES 3–5

Intermediates of Formula III which could be prepared by a Friedel-Crafts reaction of 2,6-di-t-butylphenol with known or readily prepared thiophenecarbonyl chlorides are shown in Table I.

TABLE I

| Example No. | Starting Material | Compound of Formula III |
|---|---|---|
| 3 | 2-chlorocarbonyl-5-bromo-thiophene structure | 3,5-di-tert-butyl-4-hydroxyphenyl (5-bromo-thien-2-yl) ketone |
| 4 | 2-chlorocarbonyl-3-bromo-thiophene structure | 3,5-di-tert-butyl-4-hydroxyphenyl (3-bromo-thien-2-yl) ketone |
| 5 | 3-chlorocarbonyl-5-bromo-thiophene structure | 3,5-di-tert-butyl-4-hydroxyphenyl (5-bromo-thien-3-yl) ketone |

EXAMPLES 6–8

Using the general method of Part B of Example 1, the bromo intermediates of Formula III indicated in Table II could be converted to the nitrile intermediates of Formula II which are also indicated in Table II.

TABLE II

| Example No. | Intermediate of Formula III | Intermediate of Formula II |
|---|---|---|
| 6 | Example 3 | 3,5-di-tert-butyl-4-hydroxyphenyl (5-cyano-thien-2-yl) ketone |
| 7 | Example 4 | 3,5-di-tert-butyl-4-hydroxyphenyl (3-cyano-thien-2-yl) ketone |
| 8 | Example 5 | 3,5-di-tert-butyl-4-hydroxyphenyl (5-cyano-thien-3-yl) ketone |

EXAMPLES 9–11

Using the method of Part C of Example 1, the nitrile intermediates of Formula II indicated in Table III could be hydrolyzed to the compounds of Formula I shown in Table III.

TABLE III

| Example No. | Intermediate of Formula II | Product of Formula I |
|---|---|---|
| 9 | Example 6 | 3,5-di-tert-butyl-4-hydroxyphenyl (5-carboxy-thien-2-yl) ketone |
| 10 | Example 7 | 3,5-di-tert-butyl-4-hydroxyphenyl (3-carboxy-thien-2-yl) ketone |
| 11 | Example 8 | 3,5-di-tert-butyl-4-hydroxyphenyl (5-carboxy-thien-3-yl) ketone |

What is claimed is:

1. A compound of the formula

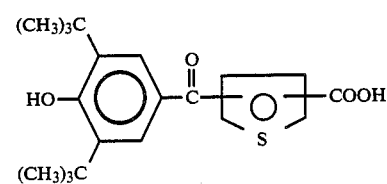

or a derivative thereof selected from a lower alkyl ester, a (lower)alkylamino(lower)alkyl ester, a pharmaceutically acceptable (lower)alkylamino(lower)alkyl ester acid-addition salt and a pharmaceutically acceptable carboxylate salt.

2. A compound according to claim 1, wherein the carboxyl is on the 5 position of the thiophene ring.

3. A compound according to claim 1, wherein the linking carbonyl is on the 2 position of the thiophene ring.

4. 5-(3',5'-di-t-butyl-4'-hydroxybenzoyl)thiophene-2-carboxylic acid according to claim 1.

5. A compound of the formula

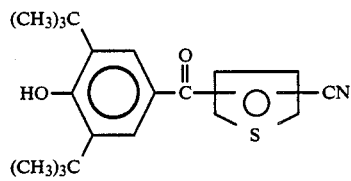

6. A method for inhibiting bronchoconstriction due to an allergic reaction in a mammal comprising administering a compound according to claim 1 to said mammal in an amount effective to inhibit said bronchoconstriction.

7. An antiallergic pharmaceutical composition comprising a compound according to claim 1 and a pharmaceutically acceptable carrier, said compound being present in an amount sufficient for providing an antiallergic response.

8. A method for inhibiting leukotriene synthesis in a mammal comprising administering a compound according to claim 1 to said mammal in an amount effective to inhibit said synthesis.

9. A method for inhibiting lipoxygenase activity in a mammal comprising administering a compound according to claim 1 to said mammal in an amount effective to inhibit said activity.

* * * * *